United States Patent [19]

Moreno et al.

[11] Patent Number: 5,395,325
[45] Date of Patent: Mar. 7, 1995

[54] DOUBLE CHAMBER DISPOSABLE SYRINGE

[76] Inventors: Saul Moreno; Jaime L. Szapiro; Leonardo Szames, all of Tabare 1641, Buenos Aires, Argentina

[21] Appl. No.: 176,470

[22] Filed: Jan. 3, 1994

[30] Foreign Application Priority Data

Mar. 10, 1993 [AR] Argentina .................. 324463

[51] Int. Cl.⁶ ........................................ A61M 5/00
[52] U.S. Cl. .................................. 604/89; 604/191
[58] Field of Search .............. 604/89, 88, 87, 86, 604/191, 198, 218, 231, 232, 187, 110

[56] References Cited

U.S. PATENT DOCUMENTS

| | | | |
|---|---|---|---|
| 4,702,737 | 10/1987 | Pizzino | 604/191 |
| 4,886,495 | 12/1989 | Reynolds | 604/88 |
| 4,941,876 | 7/1990 | Meyer et al. | 604/89 |
| 4,969,877 | 11/1990 | Kornberg | 604/198 X |
| 5,015,229 | 5/1991 | Meyer et al. | 604/191 X |

*Primary Examiner*—John D. Yasko
*Attorney, Agent, or Firm*—Bachman & LaPointe

[57] ABSTRACT

Syringe for medical use having two chambers for containing powdered drug and diluent. Its construction is practical and economical, being also disposable.

8 Claims, 2 Drawing Sheets

DOUBLE CHAMBER DISPOSABLE SYRINGE

FIELD OF THE INVENTION

The instant invention relates to a double chamber disposable syringe for simultaneous dilution and administration of powdered drugs, of the type marketed with the product to be injected contained therein, all parts and forming elements thereof being duly sterilized, such that, the user may not contact the medicine, or the needle and surrounding regions, before, during and after effecting the injection. In this case, powdered drugs may be used which are diluted at the moment of injection, resulting in several advantages which will be detailed hereinbelow.

BACKGROUND OF THE INVENTION—PRIOR ART

More particularly, the instant invention relates to a syringe of the above mentioned type comprised by a main cylindrical, hollow body, containing the medicine to be administered, and through which a coaxial plunger is located. In all cases the lower base of said main cylindrical body has an opening through which the rear end of said coaxial plunger projects, and having an annular flange in order that the user may push or pull manually the plunger, according to the desired action. The inner end or head of the plunger tightly fits inside the walls and at the bottom of said main body, such that the variable volume chamber defined therein is always tight and isolated from the outside. Said bottom has, in turn, an outer frusto-conical hollow and coaxial nozzle converging towards its outer end, constituting the plugging means for coupling and fixing the injection needle.

The novelty of the invention resides in that the syringe has two chambers: one containing the powdered product and the other the diluent. i.e. it is capable of diluting and administering simultaneously powdered drugs.

Such a functional feature, in a disposable syringe, is a consequence of various novel constructive characteristics.

It is known that, at present, administration of powdered drugs requires prior preparation of the mixture before introducing it into the syringe, this implying contamination risks even though this procedure is carried out carefully; in order to be diluted, such powdered drugs are subject to handling which may introduce contaminants, said handling comprising solid and solvent pouring from one container to another and then introducing the mixture into the syringe.

The instant invention always warrants the use of new syringes and needles, thus preventing any possibility of contamination during preparation, as a consequence of the elimination of steps and containers used for preparing and administering this kind of medicines, the operation being carried out completely inside the syringe, in a single step.

The invention also affords a quick operation since preparation and application times are shortened, assuring at the same time the exact dosage of the drug. It also avoids accidental cuts on the user's fingers since powdered drug and solvent glass containers are not employed.

The above mentioned advantages are a result of the novel syringe of the invention, which has a main body defining two aligned and coaxial chambers, from which that closer to the needle contains the powdered drug, and the second is a hollow cylinder body tightly displacing through the inner part of the former chamber and including the liquid diluent. Further, through the interior of this second chamber, the syringe plunger displaces; between both chambers there is a elastomeric and tight plug, integral to the lower chamber body, tightly and slidably fitted on the inner cylindrical surface of the upper chamber body. This plug has a longitudinal central conduit communicating both chambers such that liquid contained in the lower chamber may penetrate the upper chamber when the syringe plunger is actuated, the mixture obtained is stirred until total dilution of the solid occurs; then injection is effected by continuously pushing the plunger which, at this time, also displaces said longitudinal central plug.

BRIEF DESCRIPTION OF THE DRAWINGS

A preferred, non-limiting, embodiment of the invention will be hereinbelow described in connection with the accompanying drawings, in which.

In all figures, the same reference numerals designate the same or equivalent elements.

DETAILED DESCRIPTION OF THE INVENTION

Figure 1:
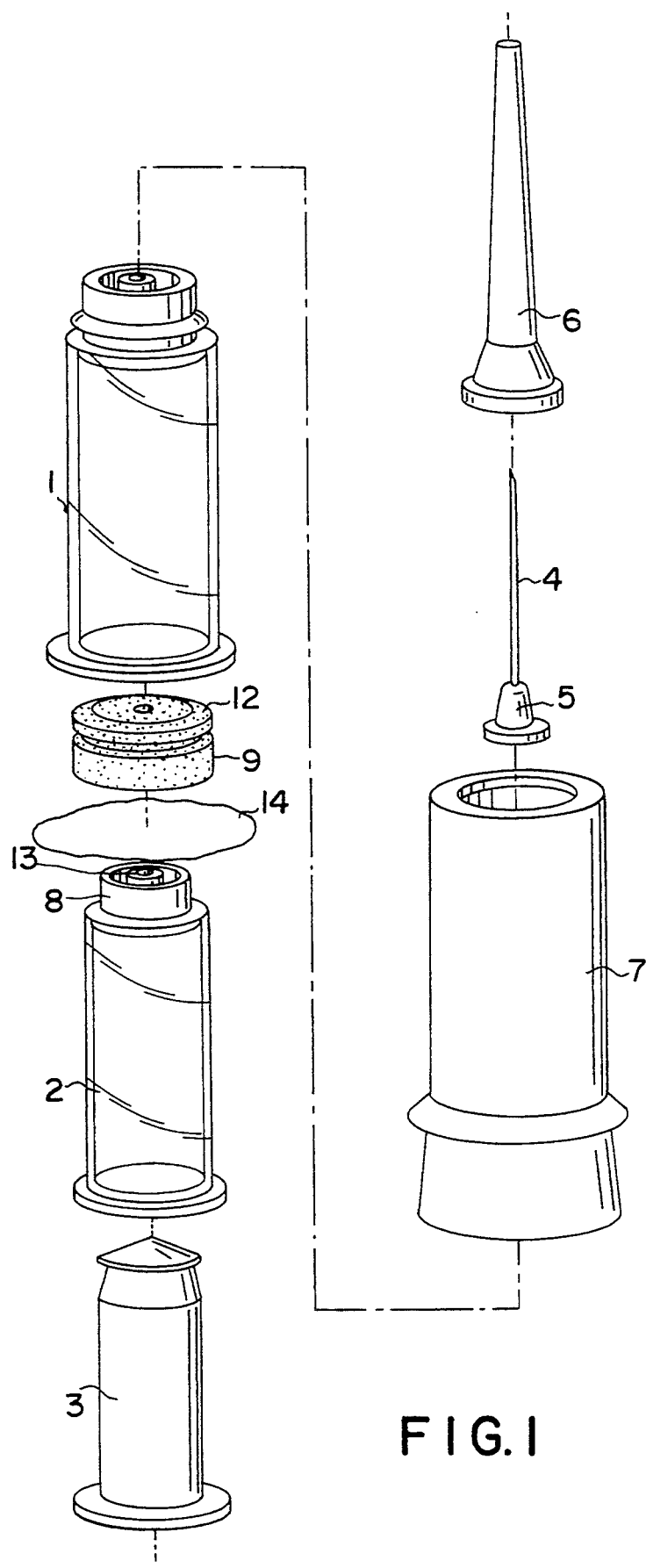
FIG. 1 is a schematic exploded perspective view of a syringe of the invention.

As shown by the drawings, the syringe of the invention is comprised by a first chamber body 1, a second, slidable, chamber body 2, a thrust plunger 3, an injection needle 4 having its plugging cone 5 and its sheath 6; a needle cover skirt 7 slidable with respect to said chamber body 1.

The novelty of the invention resides in the use of two chambers 10 and 11 which allows the pre-filling of the disposable syringe with powdered drug and diluent.

Figure 2:
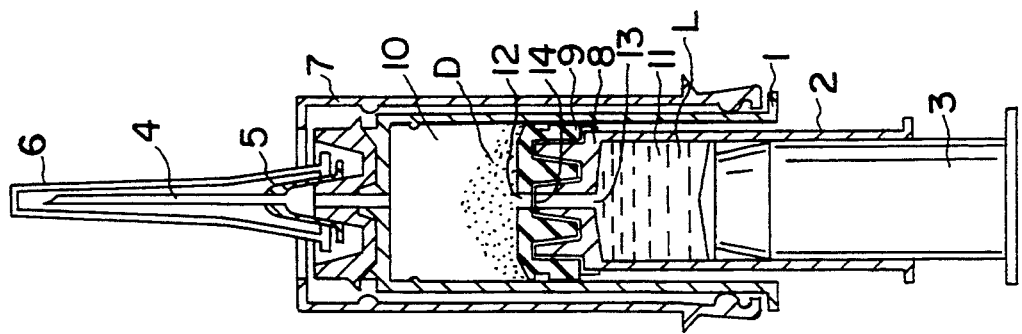
FIG. 2 is a schematic longitudinal section of the syringe of FIG. 1, showing the arrangement of the forming elements before use.

In fact, as may be seen in FIG. 2, the syringe of the invention may be marketed with the medicine already contained therein, i.e. the solid drug (powder) D inside chamber 10 and the diluent liquid L inside chamber 11.

In order that the assembly may operate properly, the upper base of the chamber body 2 has a coupling head 8 wherein the elastomeric plug is press-fitted, such plug being tightly fitted in the cylindrical wall of the chamber body 1 thus, said plug 9 serves as supporting means for the chamber body 2 and plunger 3 and also as tight division for both chambers 10 and 11.

Said plug 9 as well as the coupling head 8 have corresponding coaxial conduits 12 and 13 for communicating both chambers, blocked by brittle sheet 14 when products D and L are housed into their corresponding chambers (FIG. 2), before being mixed and diluted to be injected.

Figure 3:
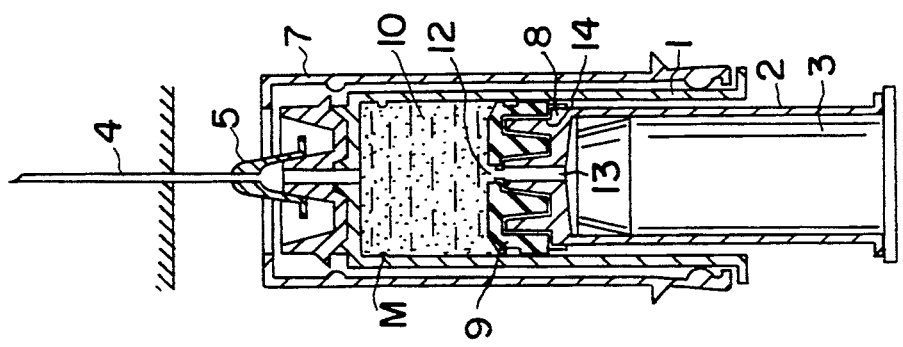
FIG. 3 is a section similar to that of FIG. 2 showing the arrangement of the forming elements once the product mixture (solid-diluent) is produced.

Thus, the use, before injecting the drug, should displace plunger 3 until the compressed liquid L collapses the separating sheet 14 at the portion between the two coaxial conduits 12 and 13. Said plunger 3 should displace until is head 15 abuts the upper base of chamber 2, whereby leak or feedback of mixture M contained in the body 1 is prevented, as shown in FIG. 3.

Once the mixture is at said body 1, the user stirs the syringe until the solid drug is wholly diluted. Then, the user may conventional inject the medicine, i.e. displacing plunger 3 along with the chamber body 2, the elastomeric plug 9 acting as pushing head, as may be seen in FIG. 3.

Figure 5:
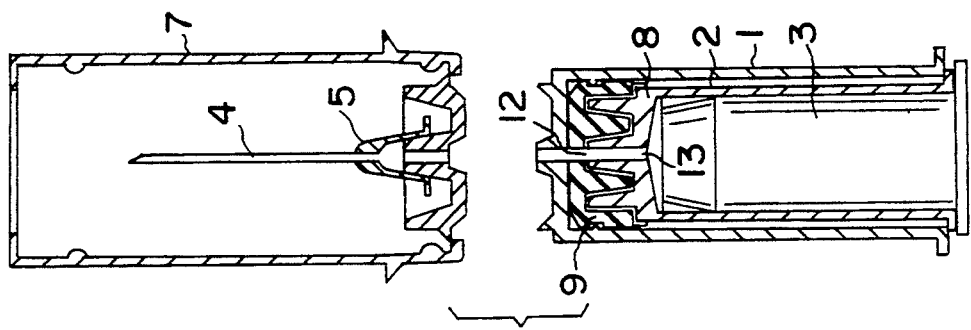
FIG. 5 is a longitudinal view showing the way in which the two main portions of the syringe of the invention are separated and disabled.
Figure 4:
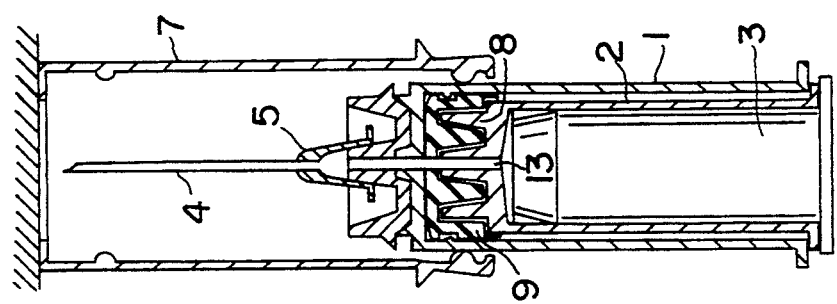
FIG. 4 is a longitudinal section as those of former figures, in this case with the needle removed after application.

The disposable character of the syringe of the invention may be clearly seen in FIGS. 4 and 5. It is also to be noted that, due to the needle cover 7, the user does not contact the needle or its surroundings.

Regarding the constructive structure of plug 9 and brittle sheet 14, both have been selected as an example to be used in the present embodiment, but equivalent alternatives may be used for the same function.

We claim:

1. A double chamber disposable syringe, comprising:
   a main hollow body having an inner diameter and engaged with an injection needle;
   a second hollow body having an outer diameter smaller than the inner diameter of the main body and having an open lower end and an upper end, wherein the upper end defines a plugging means;
   a plunger means engaged with and movable in the second body for creating a pressure in the second body, the plunger means projecting through the open lower end of the second hollow body wherein the second hollow body is positioned between the main body and the plunger means;
   a plug engaged with the inner diameter of the main body and located adjacent the plugging means, wherein the plug and plugging means have conduits in substantial alignment, the conduit of the plug leading into the main body and the conduit of the plugging means leading into the second body;
   a cylindrical needle cover extending from the main body and slidably engaged with the main body for enclosing the needle; and
   a sheet means for separating the conduits of the plug and plugging means positioned between the conduits of the plug and plugging means, wherein the sheet means is penetrable via the pressure created by the plunger means.

2. The syringe according to claim 1, wherein upon the application of the pressure against the sheet means, the sheet means is adapted to cleanly puncture without the separation of contaminable particles therefrom.

3. The syringe according to claim 2, wherein the sheet means is formed from a substantially brittle rubber.

4. The syringe according to claim 1, wherein the conduit of the plugging means has a first diameter and extends from the sheet means and into the second cylindrical body having an inner diameter substantially larger than the conduit for causing the diluting substance to enter the conduit under increased force and velocity for penetrating the sheet means.

5. A double chamber disposable syringe for simultaneous dilution and administration of a powdered drug, comprising:
   a main cylindrical hollow body adapted to contain the powdered drug, the main body having an inner wall and engaged with a removable coupling injection needle;
   a manually operated plunger means for forcibly moving a diluting substance into the main body under a pressure;
   a second cylindrical hollow body positioned between the main body and the plunger means and adapted to contain the diluting substance, the second cylindrical body having an outer diameter smaller than that of the main body and having an open lower base and an upper base, wherein the plunger means projects through the open lower base and is shiftably and tightly engaged with the second cylindrical body, and the upper base defines a coaxial plugging means;
   a cylindrical elastomeric plug adapted to substantially tightly fit in the inner wall of the main body, the plug located adjacent the plugging means, the plug and plugging means having conduits adapted to be in fluid communication;
   a cylindrical needle cover extending from the main body and having a diameter and length larger than the diameter and length of the main body; and
   a sheet means for separating the second body adapted to contain the diluting substance from the first body adapted to contain the powdered drug, the sheet means positioned between the conduits of the plug and plugging means, wherein the sheet means is penetrable via the diluting substance under the pressure provided by the plunger means.

6. The syringe according to claim 5, wherein upon the application of the diluting substance against the sheet means and under the pressure, the sheet means is adapted to cleanly puncture without the separation of contaminable particles therefrom.

7. The syringe according to claim 6, wherein the sheet means is formed from a substantially brittle rubber.

8. The syringe according to claim 5, wherein the conduit of the plugging means has a first diameter and extends from the sheet means and into the second cylindrical body having an inner diameter substantially larger than the conduit for causing the diluting substance to enter the conduit under increased force and velocity for penetrating the sheet means.

* * * * *